US00PP12885P2

(12) United States Plant Patent
Olesen et al.

(10) Patent No.: US PP12,885 P2
(45) Date of Patent: Aug. 27, 2002

(54) COMPACT FLORIBUNDA ROSE VARIETY 'POULPEACY'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 109 days.

(21) Appl. No.: 09/607,329

(22) Filed: Jun. 30, 2000

(51) Int. Cl.[7] ..... A01H 5/00
(52) U.S. Cl. ..... Plt./145
(58) Field of Search ..... Plt./145

(56) References Cited

PUBLICATIONS

UPOV–ROM GTITM Computer Database, 2001/02, GTI Jouve Retrieval Software, citation for 'POULpeacy'.*
Community Plant Variety Office "UPOV Extract" EU 4 pages.

Community Plant Variety Office "Proposal for a Variety Denomination" Jan. 26, 1999 EU 2 pages.

Community Variety Right Office "Chapter II: Variety Denominations" Apr. 15, 1999 EU 2 pages.

Community Variety Rights Office "Certificate on the Grant . . . " Jun. 19, 2000 5 pages. EU.

Canadian Food Inspection Agency "Applications Accepted for Filing" Jan. 1999 Canada 1 page.

* cited by examiner

*Primary Examiner*—Bruce R. Campell
*Assistant Examiner*—Susan B. McCormick

(57) ABSTRACT

A new compact floribunda rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

2 Drawing Sheets

SUMMARY OF THE INVENTION

The present invention constitutes a new and distinct variety of compact floribunda rose plant which originated from a controlled crossing between an unnamed seedling and an unnamed seedling. The two parents were crossed and the resulting seeds were planted in a controlled environment. The new variety is named 'POULpeacy'.

The new rose may be distinguished from its seed parent, an unnamed seedling, by the following combination of characteristics:

1. The unnamed seed parent has orange-yellow petals, while 'POULpeacy' has yellow ones.
2. The growth of the unnamed seedling is more vigorous than that of 'POULpeacy'.

The new variety may be distinguished from its pollen parent, an unnamed seedling, created by the same inventors, by the following combination of characteristics:

1. The yellow of the unnamed pollen parent's petals is darker than that of 'POULpeacy's petals.
2. The unnamed pollen parent's growth is more vigorous than that of 'POULpeacy'.

The objective of the hybridization of this rose variety for commercial greenhouse culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The combination of qualities of this variety represents significant improvement over previously available commercial cultivars of this type and distinguishes 'POULpeacy' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULpeacy' was selected by the inventors as a single plant from the progeny of the hybridization in Fredensborg, Denmark.

Asexual reproduction of 'POULpeacy' by cuttings and traditional budding was first done by L. Pernille and Mogens N. Olesen in Fredensborg, Denmark. This initial and other subsequent propagations conducted in controlled environments have demonstrated that the characteristics of 'POULpeacy' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULpeacy'. Specifically illustrated in SHEET 1:

1. Stem or entire plant showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULpeacy', as observed in its growth in glasshouses in Burlington, Canada; Half Moon Bay, Calif., and in a field nursery in Jackson County, Oreg., on plants aged 14 weeks. Color references are made using The Royal Horticultural Society (London, England) Colour Chart, 1995, except where common terms of color are used.

For a comparison, several physical characteristics of the rose variety 'POULdace', a miniture rose variety from the same inventors described and illustrated in U.S. Plant patent application Ser. No. 09/165,408 dated Oct. 2, 1998 are compared to 'POULpeacy' in Chart 1.

CHART 1

| | 'POULpeacy' | 'POULdace' |
|---|---|---|
| Petal Count | Double; 34 to 38 Petals | Semi-Double; 15 to 20 Petals |
| Open Bloom, Upper Surface of Outermost petals. | Yellow Group 13B | Yellow Group 9B |
| Open Bloom, Petal Color, Reverse Side of Outermost Petals. | Yellow Group 13B | Yellow Group 9C |

Parents

Classification:

*Botanical.*—*Rosa hybrida.*

*Commercial.*—*Compact Floribunda.*

FLOWER AND FLOWER BUD

Blooming habit: Continuous.

Flower bud:

*Size.*—Upon opening, 25 mm to 35 mm in length from base of receptacle to end of bud.

*Bud form.*—Pointed ovoid.

*Bud color.*—As sepals unfold, Yellow Group 5B, (with some guard petals having intonations of Green Yellow Group 1B) to Yellow Group 12B at ¼ opening.

*Sepals.*—Sepals are 30–33 mm long and 10 mm wide. Sepal coloration is Green Group 137C. Medium to strong foliaceous appendages on three of the sepals. Some appendages 8 mm long, with feathered ends. Surfaces of sepals slightly pubescent. Limited number of stipitate glands present on margins of sepals. More pubescence on margins than observed on inside surface of sepal.

*Receptacle.*—Surface: Smooth. Shape: Funnel. Size: 6 to 8 mm (h)×10 mm (w). Color: Yellow-Green Group 144A.

*Peduncle.*—Surface: Smooth. Length: 40 to 60 mm average length. Color: Yellow Green Group 144A. Strength: Upright.

*Borne.*—Generally with 1 to 2, and occasionally 3, buds per flowering stem.

Flower bloom:

*Fragrance.*—Light; fruit-like scent.

*Duration.*—As a pot plant, flowers last from 14 to 21 days. As a cut flower 3 to 4 days.

*Size.*—Large for a 15 cm pot rose. Average flower diameter is 40 to 60 mm when open.

*Form.*—Shape of flower when viewed from the side: Upon opening, upper part: Flattened convex to convex. Upon opening, lower part: Flattened convex. Open flower, upper part: Flattened convex. Open flower, lower part: Flattened convex.

*Petalage.*—Very double; Average rang of 45 to 50 petals under normal conditions with 6 to 12 petaloids.

Color:

*Upon opening, petals.*—Outermost petals: Upper Surface: Yellow Group 13A to Yellow Group 13B in the middle zone. In the marginal zone, Yellow Group 13B to Yellow-Orange Group 15A and B. Reverse Side: Yellow Group 13C. Innermost petals: Upper Surface: Yellow Group 13A to Yellow Group 13B. Reverse Side: Yellow Group 13B.

*Upon opening, basal petal spots.*—No distinctive coloration at petal base observed.

*After opening, petals.*—Outermost petals: Upper Surface: Yellow Group 9A in the basal and middle portions of the petal; the margins appear as Yellow Group 4D. Reverse Side: Yellow Group 9C. Innermost petals: Upper Surface: Yellow Group 9B at base of petal and Yellow Group 9C in middle and margin of petal. Reverse Side: Yellow Group 9B to Yellow Group 9C.

*Upon opening, basal petal spots.*—No distinctive coloration at petal base observed.

General tonality: On open flower Yellow Group 9B. No change in the general tonality of the flower as it ages.

Petals:

*Petal reflex.*—Moderate petal reflex. Outermost petals double reflexed.

*Petal margin.*—Uniform, with inner petals slightly undulated.

*Shape.*—Round.

*Petaloids.*—Present; quantity: 6 to 12.

*Thickness.*—Average.

*Petal size.*—20 to 26 mm (w)×26 to 32 mm (h).

*Arrangement.*—Imbricated.

Reproductive organs:

*Pollen.*—Color: Greyed Orange Group 164B and C. Quantity: Average.

*Anthers.*—Size: 2 mm. Color: Yellow-Green Group 145C to Green Yellow Group 1C. Quantity: 35 to 40.

*Filaments.*—Color: Yellow-Orange Group 15A. Length: 5–6 mm.

*Stigmas.*—Superior in location to anthers. Color: Green Yellow Group 1B.

*Styles.*—Length: 6 to 7 mm. Color: Yellow-Green Group 145C.

PLANT

Plant growth: Vigorous, compact, upright. When grown as a 15 cm pot plant, the average height of the plant itself is to 24 to 28 cm and the average width is 24 to 28 cm.

Stems:

*Color.*—Young wood: Green Group 137 A and B. Older wood: Green Group 137A and B.

*Thorns.*—Incidence: Moderate number in mid to lower half of stems. Upper half of stem nearly thornless. Size: Average length: 3 to 8 mm. Color: Yellow-Green Group 145C at base with upper half having intonation of Greyed Red Group 181C. Shape: Linear.

*Surface.*—Young wood: Smooth. Older wood: Smooth.

*Length.*—Under typical greenhouse production conditions, stem length is 25 to 30 cm. Internode length varies from 8 to 10 cm.

Plant foliage: Normal number of leaflets on normal leaves in middle of the stem: 5 leaflets.

*Leaf size.*—Large; 95 to 115 mm (l)×70 to 90 mm (w).

*Quantity.*—Very abundant.

*Color.*—Upper Leaf Surface: Green Group 139A. Lower Leaf Surface: Green Group 137C. Juvenile foliage: Upper leaf surface is Green Group 137A to Green Group 139A. Lower leaf surface is Green Group 138A. Anthocyanin intonation: Yes. Location: Margin of leaflet, upper petiole. Color: Greyed-Purple Group 184A.

Plant leaves and leaflets:

*Stipules.*—Size: 6 to 7 mm. Color: Green Group 137C. Presence of stipitate glands: Very limited number observed.

*Petiole.*—Length: 20 to 25 mm. Color: Green Group 137C. Underneath: Limited with a few, small prickles. Color is Yellow-Green Group 145D. Margins: Moderate number of stipitate glands observed.

*Rachis.*—Color: Green Group 137C. Underneath: Small prickles present every 10 to 15 mm. Some stipitate glands present. Margins: Moderate number of stipitate glands observed.

*Leaflet.*—Edge: Serrated. Shape: Ovate. Other: Moderately glossy. Leathery; of average thickness.

Disease resistance: Above average resistance to mildew, black spot, and Botrytis under normal growing conditions in Half Moon Bay, Calif., and Fredensborg, Denmark.

Cold hardiness: 'POULpeacy' has been found to be resistant to damage from cold, heat and drought damage in USDA Zone 7.

We claim:

1. A new and distinct variety of compact floribunda rose plant, substantially as herein illustrated and described as a distinct and novel rose variety due to its abundant yellow flowers, vigorous and compact growth, year round flowering under glasshouse conditions, suitability for production from softwood cuttings in pots, and durable flowers and foliage which make the variety suitable for distribution in the floral industry.

* * * * *

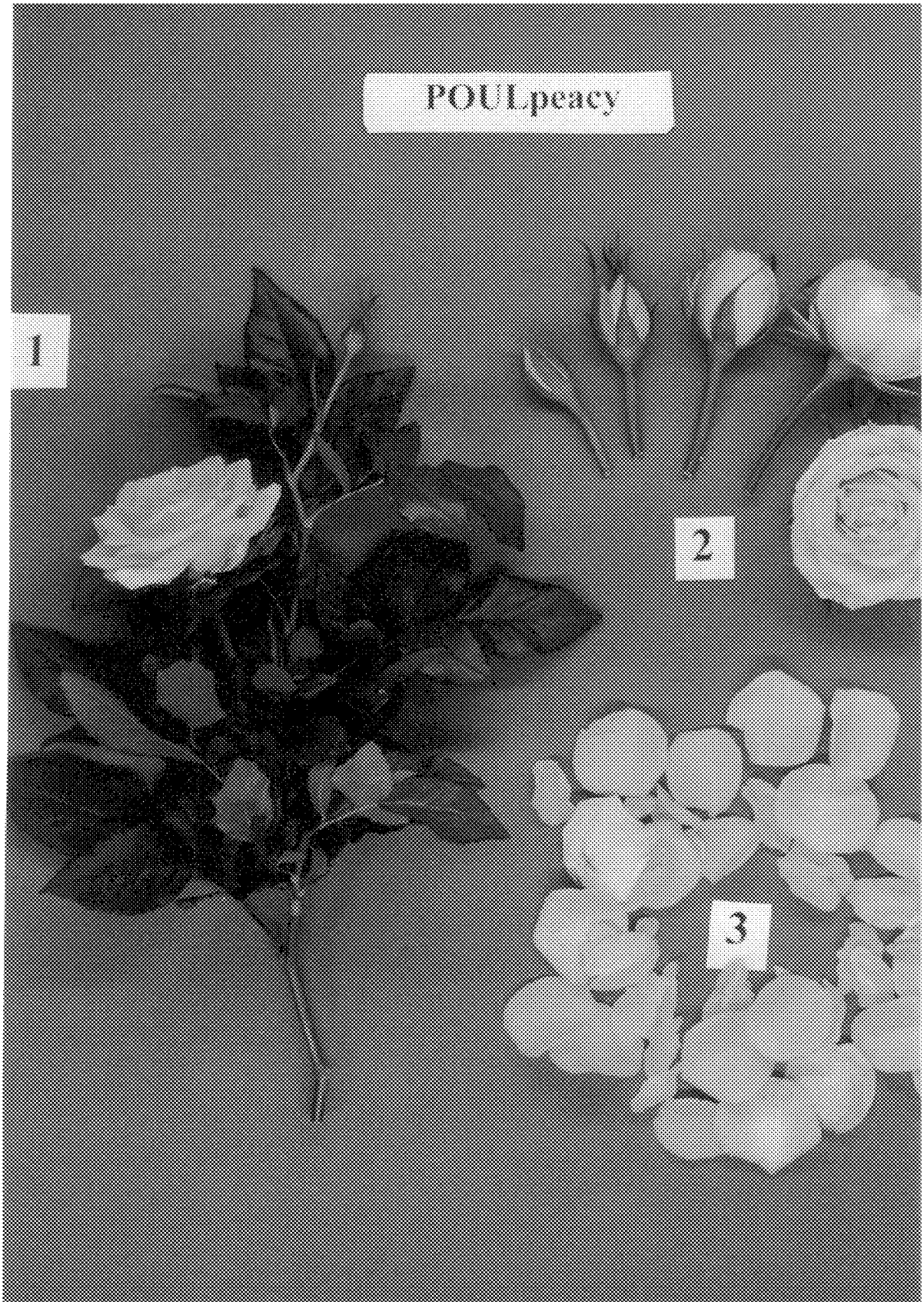
POULpeacy
1
2
3

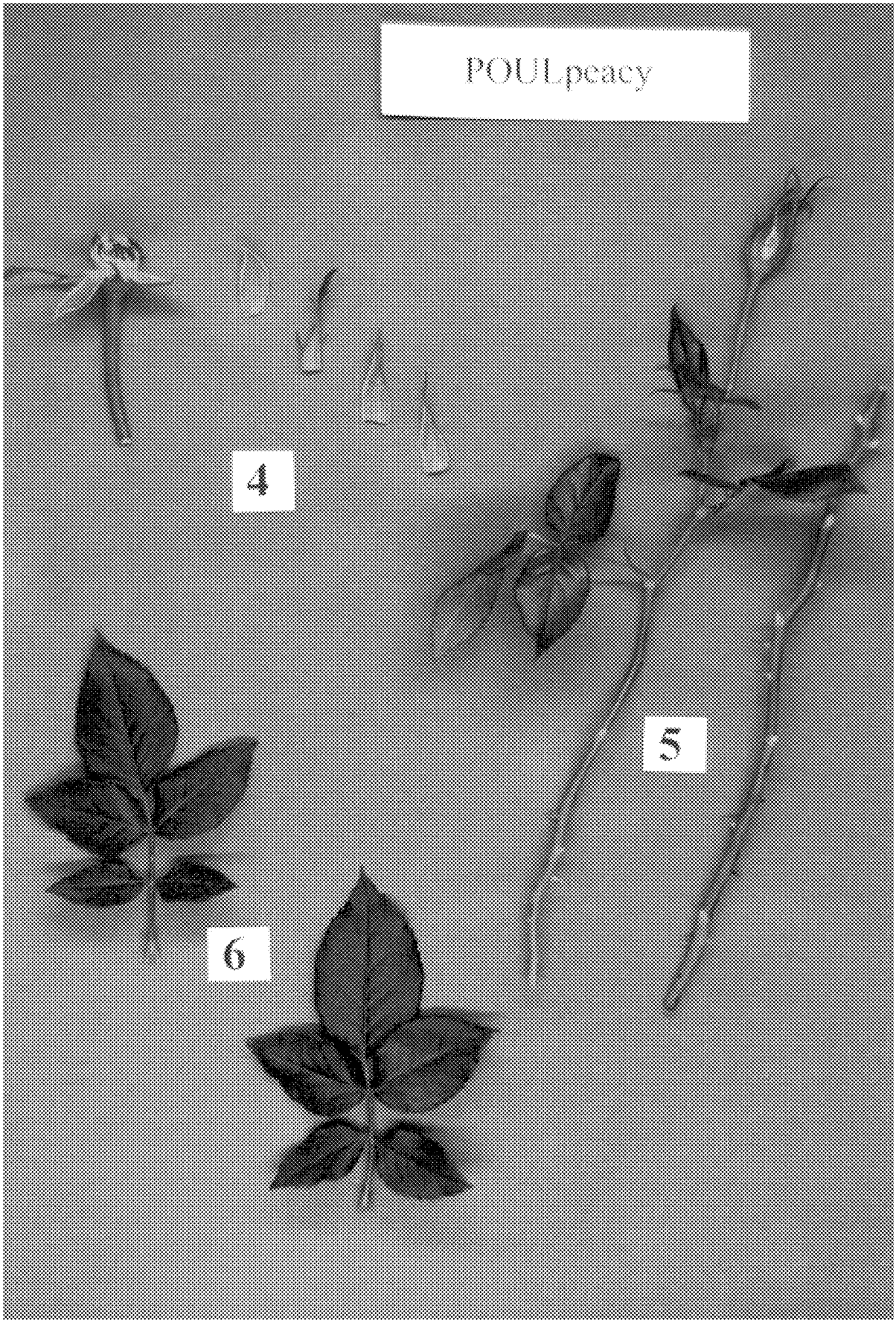
POULpeacy
4
5
6